United States Patent [19]

Scholl et al.

[11] 4,267,353

[45] May 12, 1981

[54] PREPARATION OF AROMATIC URETHANES

[75] Inventors: Hans-Joachim Scholl, Cologne; Armin Zenner, Dormagen, both of Fed. Rep. of Germany

[73] Assignee: Bayer Aktiengesellschaft, Leverkusen, Fed. Rep. of Germany

[21] Appl. No.: 69,020

[22] Filed: Aug. 22, 1979

[30] Foreign Application Priority Data

Sep. 6, 1978 [DE] Fed. Rep. of Germany ....... 2838754

[51] Int. Cl.³ .............. C07C 125/063; C07C 125/065; C07C 125/07; C07C 125/073
[52] U.S. Cl. ........................................ 560/24; 560/25; 560/27; 560/28; 560/30; 560/31; 560/32; 252/428
[58] Field of Search ...................... 560/24, 30, 25, 27, 560/28, 31, 32

[56] References Cited

U.S. PATENT DOCUMENTS

| | | |
|---|---|---|
| 3,895,054 | 7/1975 | Zajacek et al. ...................... 560/24 |
| 3,993,685 | 11/1976 | Zajacek et al. ...................... 560/24 |
| 4,080,365 | 3/1978 | Hirai et al. .......................... 560/24 |
| 4,134,880 | 1/1979 | Miyata et al. ....................... 560/24 |
| 4,170,708 | 10/1979 | Hirai et al. .......................... 560/24 |

FOREIGN PATENT DOCUMENTS 1472243 5/1977 United Kingdom .
1485108 9/1977 United Kingdom .

*Primary Examiner*—G. T. Breitenstein
*Attorney, Agent, or Firm*—Gene Harsh; Joseph C. Gil; Lyndanne M. Whalen

[57] ABSTRACT

This invention relates to an improved process for the preparation of urethanes by the reaction of aromatic nitro compounds with alcohols and carbon monoxides in the presence of catalyst systems containing sulphur and/or selenium and/or compounds of these elements.

7 Claims, No Drawings

PREPARATION OF AROMATIC URETHANES

BACKGROUND OF THE INVENTION

Previously, urethanes were generally prepared by the reaction of an aromatic isocyanate with an alcohol. The aromatic isocyanate was usually obtained by the reaction of phosgene with the appropriate primary amine. This primary amine, in turn, was generally obtained by reduction of the corresponding nitro compound. This conventional process has various disadvantages, not the least of which is the toxicity and corrosive nature of phosgene and the formation of hydrogen chloride as a by-product. Also, it is known that certain aromatic amines have harmful biological properties and some of them tend to be oxidized by air during storage.

There have, therefore, been several attempts to avoid the use of highly toxic phosgene and obtain urethanes directly from the corresponding nitro compounds, the corresponding alcohols and carbon monoxide. The processes according to U.S. Pat. No. 3,993,685 and British Pat. No. 1,472,243 use catalyst systems based on metals of the platinum group. Since the loss of very expensive catalysts is inevitable, these processes have not been used on a large commercial scale.

In the process according to U.S. Pat. No. 3,895,054, it is proposed to use a combination of selenium or sulphur or compounds of these elements with very large quantities of a base as the catalytically active system. The bases which may be used include, for example, triethylamine and pyridine. In order to obtain a satisfactory start to the reaction in the presence of these amines, it appears necessary to use rather large quantities of tertiary amines in relation to the nitro compounds used as the starting material. In fact, if dinitrotoluene is used as the nitro compound, the quantity of tertiary amine used is equal to, or greater than, that of the dinitrotoluene. The use of such large quantities of a tertiary amine entails numerous economic and recovery problems. Moreover, this process leads to the formation of by-products, such as amino compounds and ureas, if measurable quantities of water are present, e.g. as hydrates or in the free form. This process is, therefore, also unsuitable for large scale industrial application.

The reduction in the yield of the desired urethanes due to the above-mentioned formation of by-products can be prevented. According to British Pat. No. 1,485,108 the use of a catalyst system which is composed of elementary selenium or a selenium compound and a promoter consisting, for example, of a bicyclic amidine and a carboxylic acid, increases the yield. Although this process provides higher yields of urethanes it also leads to disturbing quantities of by-products which constitute the products of hydrolysis and secondary reactions of the urethane formed.

The process of U.S. Pat. No. 4,080,365 must be regarded as a further development in that the formation of by-products from urethane is suppressed through the use of aromatic urea compounds of aromatic amino compounds correspondings to these by-products. Although this measure provides an improvement it still has serious disadvantages. In particular, it requires the use of exceptionally large quantities of selenium or selenium compounds so that large quantities of this catalyst are lost. Moreover, selenium or the selenium compounds used as catalysts are not entirely acceptable toxicologically and in addition impart an unpleasant odor to the urethane produced.

It is therefore an object of the present invention to provide an improved process for the preparation of urethanes from aromatic nitro compounds, alcohols and carbon monoxide which could be carried out either entirely without selenium or selenium compounds or with much smaller quantities of these substances and still provide quantitive formation of urethane.

DESCRIPTION OF THE INVENTION

This could surprisingly be solved by the process according to the present invention which is described in more detail below, wherein the problems of purification, toxicity and separation described above are largely eliminated.

This invention relates to a process for the preparation of urethanes by the reaction of aromatic nitro compounds with aliphatic, cycloaliphatic or araliphatic alcohols and carbon monoxide in the presence of;

(a) sulphur and/or selenium and/or compounds of these elements, (b) aromatic amino compounds and/or aromatic urea compounds and (c) tertiary organic amines and/or alkali metal salts of weak acids, wherein the catalyst system used contain as additional components:

(d) oxidizing agents selected from the group consisting of oxygen, oxidizing organic compounds containing chemically bound oxygen and oxidizing inorganic compounds of metals of the First, Second and Fifth to Eighth sub-Groups of the Periodic System of Elements containing chemically bound oxygen and (e) ammonia and/or aliphatic araliphatic, cycloaliphatic or heterocyclic amines having at least one hydrogen atom attached to an amine nitrogen atom.

Suitable aromatic nitro compounds, for use in the instant invention include, e.g. nitrobenzene, 4-nitrochlorobenzene, 3,4-dichloronitrobenzene, 1,3-dinitrobenzene, o-nitrotoluene, m-nitrotoluene, p-nitrotoluene, 2,4-dinitrotoluene, 2,6-dinitrotoluene, nitronaphthalenes, nitroanthracenes, dinitrobiphenylenes, and the like. Nitro compounds which are suitable for the process of the present invention generally have a molecular weight of from 123 to 300 and contain from 1 to 3 aromatic nuclei and from 1 to 3 nitro groups attached to aromatic nuclei and optionally other substituents which are inert under the reaction conditions of the process according to the invention. Among the preferred nitro compounds for the process according to the present invention are included nitrobenzene and the above-mentioned dinitrotoluenes. Any mixtures of the aforesaid nitro compounds may, of course, also be used.

Suitable aliphatic, cycloaliphatic or araliphatic alcohols, include preferably any organic compounds having a molecular weight of from 32 to 300 which have at least one aliphatically, cycloaliphatically or araliphatically bound hydroxyl group and are otherwise inert under the reaction conditions. Examples of suitable alcohols include ethanol, n-propanol, isopropanol, the various isomeric butanols, cyclohexylalcohol, benzyl alcohol, hexyl alcohol, lauryl alcohol, cetyl alcohol and the like. Monohydric alcohols are preferably used in the process according to the present invention, and ethanol and methanol are particularly preferred. Gaseous carbon monoxide is used in the instant invention.

Suitable catalyst systems used according to the present invention, contain (a) sulphur and/or selenium and- /or compounds of these elements, (b) aromatic amino compounds and/or aromatic urea compounds, (c) at least one tertiary organic amine and/or at least one alkali metal salt of a weak acid, (d) certain oxidizing agents to be described in more detail below and (e) ammonia and/or at least one aliphatic, araliphatic, cycloaliphatic or heterocyclic amine having at least one hydrogen atom attached to an amine nitrogen.

Suitable catalyst components (a) include, a(2) elementary sulphur in any form, inorganic or organic compounds, preferably of divalent sulphur, e.g. carbonyl sulphide (COS), hydrogen sulphide, alkali metal sulphides such as sodium sulphide, dimethylsulphide, diethylsulphide, thiophene or thiourea. Elementary sulphur, carbonyl sulphide and sulphur compounds which form carbonyl sulphide in situ under the reaction conditions of the process according to the present invention are preferred. Also suitable are, a(2) selenium in any form, preferably metallic selenium, or inorganic selenium compounds such as selenium dioxide or carbonyl selenide (COSe). One could conceivably also use organic selenium compounds, e.g. dimethyl selenide, diphenylselenide or the like. Among the co-catalysts mentioned, elementary selenium is particularly preferred. Sulphur is most particularly preferred.

Catalyst components (b) may be any organic compounds which have aromatically bound primary amino groups and/or aromatically bound urea groups and which in addition to these groups may also contain nitro groups and urethane groups. Component (b) of the catalyst system according to the instant invention is generally a compound or mixture of compounds corresponding to the following general formulae:

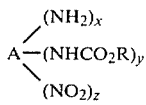

and or

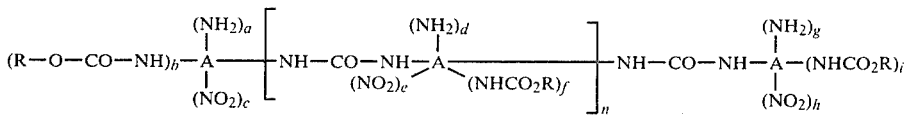

wherein
x represents 1 or 2,
y represents 0 or 1,
z represents 0 or 1 and the sum of x+y+z is preferably 1 or 2;
a,b,c,d,e,f,g,h and i each represent 0 or 1 and the sum of a+b+c is equal to the sum of g+h+i and is 0, 1 or 2; when a+b+c=1 or 2, the sum of d+e+f is less than this value by 1, i.e. 0 or 1, and when a+b+c=0, d+e+f is also 0;
represents 0, 1, 2 or 3, preferably 0;
A represents a monovalent, divalent or trivalent, preferably a monovalent or divalent aromatic hydrocarbon group which is optionally substituted with a $C_1$–$C_4$-alkyl group and otherwise preferably corresponds to the aromatic hydrocarbon group of the aromatic nitro compound used in the instant invention, and
R represents an aliphatic, cycloaliphatic or araliphatic hydrocarbon group generally having up to 18 carbon atoms and which in other respects preferably corresponds to the hydrocarbon group of the alcohol component used in the instant invention.

The following are examples of suitable catalyst components (b): aniline; o-, m- or p-toluidine; the isomeric nitroanilines; the isomeric diaminobenzenes; N,N'-diphenylurea; N,N'-bis-(2-methyl-5-nitro-phenyl)-urea; N,N'-bis-(2-methyl-5-ethoxycarbonylamino-phenyl)-urea; N,N'-bis-(2-methyl-5-amino-phenyl)-urea; 2-amino-4-nitrotoluene; 4-amino-2-nitrotoluene; 2-amino-4-ethoxycarbonylamino-toluene; 4-amino-2-ethoxycarbonylamino-toluene; 2,4-diaminotoluene; N,N'-bis-(3-nitro-4-methylphenyl)-urea; N,N'-bis-(2-methyl-5-nitrophenyl)-urea; N,N'-bis-(3-ethoxycarbonylamino-4-methylphenyl)-urea; N,N'-bis-(2-methyl-5-ethoxycarbonylamino-phenyl)urea; N,N'-bis-(3-amino-4-methylphenyl)-urea; N,N'-bis-(2-methyl-5-aminophenyl)-urea; N-(3-nitro-4-methylphenyl)-N'-(2-methyl-5-nitrophenyl)-urea; N-(3-ethoxycarbonylamino-4-methylphenyl)-N'-(2-methyl-5-ethoxycarbonylamino)-urea; N-(3-amino-4-methylphenyl)-N'-(2-methyl-5-aminophenyl)-urea; N-(3-nitro-4-methylphenyl)-N'-(3-ethoxycarbonylamino-4-methylphenyl)-urea; N-(3-nitro-4-methylphenyl)-N'-(2-methyl-5-ethoxy-carbonylaminophenyl)-urea; N-(3-nitro-4-methylphenyl)-N'-(3-amino-4-methylphenyl)-urea; N-(3-nitro-4-methylphenyl)-N'-(2-methyl-5-aminophenyl)-urea; N-(2-methyl-5-nitrophenyl)-N'-(3-ethoxycarbonylamino-4-methylphenyl)-urea; N-(2-methyl-5-nitrophenyl)-N'-(2-methyl-5-ethoxycarbonylaminophenyl)-urea; phenyl-urea; N-(2-methyl-5-nitrophenyl)-N'-(3-amino-4-methylphenyl)-urea; N-(2-methyl-5-nitrophenyl)-N'-(2-methyl-5-aminophenyl)-urea; N-(3-ethoxycarbonylamino-4-methylphenyl)-N'-(2-methyl-5-aminophenyl)-urea; N-(2-methyl-5-ethoxycarbonylamino-phenyl)-N'-(3-amino-4-methylphenyl)-urea; N-(2-methyl-5-ethoxycarbonylaminophenyl)-N'-(2-methyl-5-aminophenyl)-urea and any mixtures of the compounds mentioned as examples. As explained above, it is preferred to use compounds (b) which correspond in their aromatic group to the aromatic nitro compound used in the instant invention. Thus when nitrobenzene is used, for example, aniline or diphenylurea is also used. Whereas, when nitrotoluene is used, either tolylamine or a ditolylurea is used. SImilarly, when divalent nitro compounds are used, e.g. 2,4-dinitrotoluene, the corresponding compounds containing disubstituted tolyl groups are also used.

Higher homologues of the ureas given as examples may also be used, i.e. compounds containing several urea units.

Suitable catalyst components (c) are organic bases which have tertiary amino groups, e.g. tertiary aliphatic amines having a total of from 3 to 20 carbon atoms for example trimethylamine, triethylamine, N,N-dimethyloctadecylamine or trihexylamine, heterocyclic tertiary amines such as pyridine or amines which have two tertiary amino groups, e.g. diazabicyclo[2,2,2]-octane (triethylenediamine) or bicyclic amidines corresponding to the following general formula:

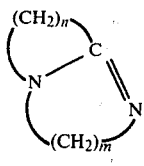

wherein n represents an integer of from 3 to 5 and
m represents an integer of from 2 to 4.

In addition to, or instead of, the above-mentioned tertiary amines, alkali metal salts of weak acids which are basic in reaction may be used as catalyst component (c), in particular alkali metal carboxylates such as sodium acetate, potassium acetate, sodium benzoate or alkali metal salts of weak inorganic acids, e.g. sodium borate or sodium carbonate can be used. Among the preferred catalyst components (c) are included, 1,5-diazabicyclo [4,3,0]-non-5-ene, 1,8-diazabicyclo[5,4,0]-undecane-7 and sodium and potassium acetate. Triethylenene-diamine is also among the preferred components, particularly in combination with salts of the following general formula:

MeX wherein

Me represents an alkali metal cation and
X represents iodide, cyanate or thiocyanate anion.

When such combinations are used, the last mentioned salts are generally used in quantities of from 1 to 40 mol %, preferably from 4 to 20 mol %, based on the nitro compound used.

The oxidizing agents (d) may be elementary oxygen or a gas which contains oxygen, (e.g. air) and/or oxidizing organic compounds containing chemically bound oxygen, (e.g. quinones, particularly 1,4-benzoquinone), and/or oxidizing inorganic compounds of metals containing chemically bound oxygen, particularly the corresponding oxides. The appropriate metal compounds of elements of the 1st, 2nd and 5th to 8th sub-Groups of the Periodic Table are preferably used. It is particularly preferred to use the corresponding compounds of elements of the 5th and 6th sub-Groups and the corresponding compounds of manganese, iron, cobalt and nickel. Examples of suitable oxidizing agents include zinc oxide, iron-II oxide, iron-III oxide, mixed oxides of the last mentioned iron oxides, vanadium-V oxide, manganese-IV oxide, molybdenum-VI oxide, nickel-II oxide, cobalt-II oxide, mixed oxides of tri- to hexavalent chromium and any mixtures of the oxides exemplified above. Iron-III oxide is one of the particularly preferred oxidizing agents. Mixed oxides containing iron, vanadium and/or molybdenum are particularly preferred.

The catalyst component (e) is ammonia and/or any aliphatic, araliphatic, cycloaliphatic or heterocyclic amine having at least one hydrogen atom bound to an amine nitrogen atom. Particularly preferred catalyst components (e) are secondary amines corresponding to the general formula:

$R_1$—NH—$R_2$ wherein $R_1$ and $R_2$ are identical or different and represent alkyl groups having from 1 to 6 carbon atoms or cycloalkyl groups having 5 or 6 carbon atoms, or $R_1$ and $R_2$ together with the secondary amine nitrogen atom may form a heterocyclic ring, preferably a 6-membered ring, which may also contain oxygen as a second hetero atom.

Suitable preferred amines include dimethylamine, diethylamine, dipropylamine, dibutylamine, methylhexylamine, dihexylamine and morpholine. Dibutylamine and morpholine are particularly preferred.

Compounds which release amine "in situ" during the process of the present invention, particularly those which release amines corresponding to the above formula $R_1$—NR—$R_2$ are, of course, also suitable as catalyst components (e). A typical example of such a class of compounds are the thioureas which undergo a well known reaction under conditions of hydrolysis to liberate the corresponding amines (see Frost Pearson, Kinetics and Mechanism, John Wiley and Sons, Inc., New York 1961), page 314):

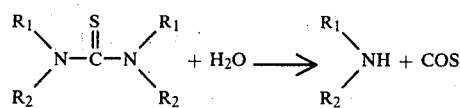

Compounds of this type are particularly interesting because any unwanted traces of water present in the reaction system are largely removed with the simultaneous formation of catalyst components which may be used according to the instant invention.

When the process according to the instant invention is carried out, the reactants are generally used in such quantities that from 1 to 50, preferably from 5 to 30 hydroxyl groups of the alcohol component are present for each nitro group of the aromatic nitro compound used as a starting material. Carbon monoxide is generally used in excess since the reaction is always carried out in a carbon monoxide atmosphere. This atmosphere may contain the proportion of oxygen required according to the instant invention.

If sulphur or sulphur compounds are used, catalyst component (a), which may be applied to a suitable carrier such as carbon, aluminum oxide, silicone dioxide, diatomaceous earth, activated clay, zeolite, molecular sieves, barium sulphate, calcium carbonate, ion exchange resins and similar materials, is used in a quantity corresponding to from 0.1 to 40% by weight, preferably from 1 to 15% by weight of sulphur in the free or bound form, based on the quantity of nitro compound used as a starting material. If selenium or a selenium compound is used, however, the catalyst component is used in a quantity corresponding to from 0.001 to 1% by weight, preferably from 0.01 to 0.5% by weight of free or bound selenium, based on the nitro compound.

The quantity of catalyst component (b), in the reaction mixture, is generally from 1 to 40 mol %, preferably from 4 to 25 mol %, based on the nitro compound used as a starting material. Catalyst component (c) is generally contained in the reaction mixture in a quantity of from 1 to 40 mole %, preferably from 4 to 25 mol % based on the nitro compound used as a starting material. These figures apply to the total quantity of basic compounds but not to the salts of the following general formula:

MeX which may also be used.

If oxygen or a gas containing oxygen is used as catalyst component (d), i.e. as the oxidizing agent, the proportion of oxygen used is from 0.01 to 6.0 volume %, preferably from 0.1 to 2 volume %, based on the carbon monoxide used. For safety reasons, the proportion of oxygen should not exceed 6.0 volume %. If oxidizing metal compounds are used, they are generally added in a quantity of from 0.1 to 100% by weight, preferably from 5 to 40% by weight, based on the nitro compound used.

Catalyst component (e) is generally present in the reaction mixture in a quantity of from 0.01 to 20 mol %, preferably from 0.1 to 15 mol %, based on the nitro compound used as a starting material.

The process according to the instant invention may be carried out in the absence of a solvent since the alcohol itself serves as a solvent. A solvent may, however, be added if desired. Examples of suitable solvents include aromatic solvents such as benzene, toluene, xylene, etc.; nitriles such as acetonitrile, benzonitrile; etc.; sulphones such as sulpholan; aliphatic halogenated hydrocarbons such as 1,1,2-tri-chloro-1,2,2-trifluoromethane; aromatic halogenated hydrocarbons such as monochlorobenzene, dichlorobenzene, trichlorobenzene, etc.; ketones, esters, and other solvents such as tetrahydrofuran, 1,4-dioxane, 1,2-dimethoxyethane and the like.

The starting materials and catalyst system may be added in any desired sequence which may be altered according to the apparatus used. For example, a starting mixture of alcohol, organic nitro compound and catalyst components (a) to (e) may be introduced into a suitable pressure resistant reactor such as an autoclave, and carbon monoxide may then be introduced under pressure and the mixture stirred, with heating, until the formation of urethane is completed. Carbon monoxide and optionally also the oxidizing agent may be introduced into the reactor either semi-continuously or continuously while the carbon dioxide formed in the reaction is removed. The reaction may be carried out batchwise, semicontinuously or continuously. The carbon monoxide present in excess after the reaction may be renewed by recirculation.

The reaction temperature is generally maintained in the range of from 80° to 220° C., preferably from 120° to 200° C. Although the velocity of the reaction increases with increasing reaction temperature, at temperatures above 220° C. thermal decomposition tends to occur which reduces the yield of urethane product. The reaction pressure, i.e. the initial carbon monoxide pressure before the reaction mixture begins to heat up, is generally in the region of from 10 to 300 bar, preferably from 20 to 150 bar. The reaction time depends on the nature of the nitro compound used, the reaction temperature, the reaction pressure, the nature and quantity of the catalyst and the nature of the apparatus. It is generally in the region of from 5 minutes to 6 hours. After termination of the reaction, the reaction mixture is either left to cool or actively cooled. After the gas introduced into the reactor has been discharged, the reaction mixture is separated by any known method by filtration, distillation or some other suitable method to isolate the urethane formed.

The reaction mixture left behind after removal of the urethane contains the catalyst system and any residues of urethane not removed. Recovery of these residues is particularly advantageous in the continuous process.

Care should be taken to exclude water when carrying out the process according to the instant invention. Since a certain amount of hydrolytic decomposition of the products in the presence of water cannot be excluded in spite of the addition of catalyst component (b).

The essential feature of the invention, in the process, according to the instant invention lies primarily, in the simultaneous use of catalyst components (d) and (e), which in combination with catalyst components (b) and (c) enable excellent catylic activity to be obtained. This is true even when selenium or selenium compounds are used as catalyst component (a) in drastically reduced quantities, compared with those previously used, and even if selenium or selenium compounds is replaced by sulphur or sulphur compounds. There is no plausible explanation at the moment for this unexpected effect of the catalyst system according to the instant invention.

The products obtained by the process according to the present invention are valuable intermediate products for the production of pesticides or of polyurethanes. They are particularly suitable for use as starting materials in the preparation of the corresponding isocyanates or polyisocyanates by the known decomposition reaction of the alcohol component.

The following Examples serve to illustrate the present invention without restricting it. All the reactions described in the Examples were carried out in a stainless steel (V 4A) autoclave equipped with stirrer. The yields given in the Examples were calculated from the results of gas chromatographic and liquid chromatographic analysis.

EXAMPLE 1

20.8 g of nitrobenzene, 2 g of sulphur, 3.21 g of aniline, 2.36 g of potassium acetate, 3 g of a metal oxide mixture of iron-III oxide and vanadium pentoxide in proportions by weight of 11:1, 2.6 g of di-n-butylamine and 169 g of absolute ethanol were introduced into a 0.7 liter autoclave. The autoclave was rinsed with nitrogen followed by carbon monoxide. Carbon monoxide was then forced into the autoclave until the starting pressure of 100 bar was reached. The reaction mixture was heated to 170° C. with stirring and then stirred for a further 2 hours at 170° C. Gas chromatographic analysis indicated quantitative conversion of nitrobenzene. The filtrate contained 20.5 g of ethyl-N-phenylcarbamate and 4.5 g of aniline.

A method of working up the reaction mixture from Eample 1 to isolate ethyl-N-phenylcarbamate is described below by way of example:

Solid constituents were filtered off and the solution was distilled to remove ethanol. The residue was taken up in 80 g toluene and the toluene extract was filtered and the filtrate shaken with water. The organic phase was distilled. After removal of toluene and residues of aniline, 21.2 g of a rapidly cyrstallizing substance distilled over at 88° to 94° C./0.2—0.3 mbar. This substance was free from other distillate impurities and according to gas chromatographic analysis consisted of 96% pure ethyl-N-phenyl carbamate.

COMPARISON EXAMPLE 1a

Example 1 was repeated without using di-n-butylamine. 43% of the nitrobenzene was converted. The filtrate contained 6.6 g of ethyl-N-phenylcarbamate and 3.7 g of aniline.

COMPARISON EXAMPLE 1b

Example 1 was repeated without using the metal oxide mixture. 70% of the nitrobenzene was converted. The filtrates contained 96 g of ethyl-N-phenylcarbamate and 3.8 g of aniline.

EXAMPLE 2

Example 1 was repeated using 1.29 g of di-n-butylamine at 160° C. for 2 hours. The nitrobenzene was converted quantitatively. The filtrate contained 22.3 g of ethyl-N-phenylcarbamate and 3.4 g of aniline.

EXAMPLE 3

Example 2 was repeated using 0.87 g of morpholine instead of di-n-butylamine. Nitrobenzene was converted quantitatively. The filtrate contained 22.2 g of ethyl-N-phenylcarbamate and 3.4 g of aniline.

COMPARISON EXAMPLE 3a

Example 3 was repeated without the addition of the metal oxide mixture. 27.4% of the nitrobenzene was converted. The filtrate contained 2.2 g of ethyl-N-phenylcarbamate and 4 g of aniline.

EXAMPLE 4

Example 3 was repeated at 180° C. for one hour. Nitrobenzene was converted quantitatively. The filtrate contained 22.9 g of ethyl-N-phenylcarbamate and 3.9 g of aniline.

EXAMPLE 5

Example 2 was repeated using 1.2 g of tetramethylthiourea instead of di-n-butylamine. Nitrobenzene was converted quantitatively. The filtrate contained 24.6 g of ethyl-N-phenylcarbamate and 2.7 g of aniline. When this reaction mixture was worked up in the manner described in Example 1, 24.4 g of ethyl-N-phenylcarbamate was obtained with a 97% degree of purity.

EXAMPLE 6

Example 5 was repeated using 0.5 g of sulphur at 170° C. for 1 hours. Nitrobenzene was converted quantitatively. The filtrate contained 21.5 g of ethyl-N-phenylcarbamate and 4.4 g of aniline.

EXAMPLE 7

51 g of nitrobenzene, 4 g of sulphur, 4 g of aniline, 2 g of potassium acetate, 4 g of a metal oxide mixture similar to that used in Example 1, 1.28 g of di-n-butylamine and 300 g of absolute ethanol were introduced into a 1.3 liter autoclave. The autoclave was rinsed with nitrogen and then with carbon monoxide. After this procedure, carbon monoxide was forced into the autoclave until the starting pressure of 100 bar was reached. The reaction mixture was heated to 180° C. with stirring and then stirred for one hour at this temperature. Gas chromatographic analysis indicated quantitative conversion of nitrobenzene. The filtrate contained 53.9 g of ethyl-N-phenylcarbamate and 8.2 g of aniline.

EXAMPLE 8

20.8 g of nitrobenzene, 2 g of sulphur, 3.21 g of aniline, 2.7 g of triethylene diamine, 2.32 g of potassium thiocyanate, 3 g of a metal oxide mixture of iron-III oxide and vanadium pentoxide in proportions by weight of 11:1, 0.87 g of morpholine and 169 g of absolute ethanol are reacted together for one hour at 180° C. as described in Example 1. Nitrobenzene was converted quantitatively. The filtrate contained 23.6 g of ethyl-N-phenylcarbamate and 4.1 g of aniline.

COMPARISON EXAMPLE 8a

Example 8 was repeated without using potassium thiocyanate. 45.7% of the nitrobenzene was converted. The filtrate contained 6.6 g of ethyl-N-phenylcarbamate and 3.3 g of aniline.

EXAMPLE 9

20.8 g of nitrobenzene, 3 g of COS, 3.21 g of aniline, 2.7 g of triethylene diamine, 2.32 g of potassium thiocyanate, 3 g of a metal oxide mixture as used in Example 8, 0.64 g of di-n-butylamine and 169 g of absolute ethanol were reacted for 2 hours at 170° C. as described in Example 1. 91.8% of the nitrobenzene was converted. The filtrate contained 21.8 g of ethyl-N-phenylcarbamate and 3.5 g of aniline.

EXAMPLE 10

51.0 g of nitrobenzene, 2 g of sulphur, 0.02 g of selenium, 4 g of aniline, 2 g of potassium acetate, 4 g of the metal oxide mixture used in Example 1, 1.28 g of di-n-butylamine and 300 g of absolute ethanol were reacted as described in Example 7. Gas chromatographic analysis indicated quantitative conversion of nitrobenzene. The filtrate contained 59.3 g of ethyl-N-phenylcarbamate and 7.3 g of aniline. When this reaction mixture was worked up as described in Example 1, it yielded 58.1 g of ethyl-N-phenylcarbamate which was 98.5% pure.

EXAMPLE 11

20.8 g of nitrobenzene, 2 g of sulphur, 3.21 g of aniline, 2.36 g of potassium acetate, 3 g of a metal oxide mixture of iron-III oxide and vanadium pentoxide in proportions by weight of 11:1, 0.87 g of morpholine and 130 g of absolute methanol were reacted as described in Example 8. Nitrobenzene was converted quantitatively. The filtrate contained 19.9 g of methyl-N-phenylcarbamate and 4.11 g of aniline.

EXAMPLE 12

20.8 g of nitrobenzene, 2 g of sulphur, 3.21 g of aniline, 2.36 g of potassium acetate, 3 g of 1,4-benzoquinone, 0.87 g of morpholine and 169 g of absolute ethanol were reacted as described in Example 8. 96.2% of the nitrobenzene was converted. The filtrate contained 18.7 g of ethyl-N-phenylcarbamate and 3.1 g of aniline.

EXAMPLE 13

Example 3 was repeated using 2.1 g of 1,8-diazabicyclo [5,4,0]-undecane-7 instead of potassium acetate. The nitrobenzene was converted quantitatively. The filtrate contained 21.3 g of ethyl-N-phenylcarbamate and 2.8 g of aniline.

EXAMPLE 14

Example 8 was repeated using 1 g of sulphur instead of 2 g of sulphur. Nitrobenzene was converted quantitatively. The filtrate contained 19.7 g of ethyl-N-phenylcarbamate and 5.0 g of aniline.

COMPARISON EXAMPLE 14a

Example 14 was repeated without using morpholine. 39.1% of the nitrobenzene was converted. The filtrate contained 5.5 g of ethyl-N-phenylcarbamate and 2.7 g of aniline.

EXAMPLE 15

Example 14 was repeated using 1.9 g of potassium cyanate instead of potassium thiocyanate. Nitrobenzene was converted quantitatively. The filtrate contained 20.7 g of ethyl-N-phenylcarbamate and 3.2 g of aniline.

EXAMPLE 16

Example 4 was repeated using 4 g of N,N,N',N'-tetramethyl-thiuramic disulphide instead of sulphur. Nitrobenzene was converted quantitatively. The filtrate contained 18.6 g of ethyl-N-phenylcarbamate and 2.9 g of aniline.

EXAMPLE 17

Example 8 was repeated but the proportion by weight of iron-III oxide to vanadium pentoxide was changed to 1:1. Nitrobenzene was converted quantitatively. The filtrate contained 18.1 g of ethyl-N-phenylurethane and 7.0 g of aniline.

EXAMPLE 18

Example 11 was repeated using 0.64 g of di-n-butylamine instead of morpholine. Nitrobenzene was converted quantitatively. The filtrate contained 20.8 g of methyl-N-phenylcarbamate and 4.0 g of aniline.

EXAMPLE 19

26.6 g of 4-nitrochlorobenzene, 2.0 g of sulphur, 0.2 g of metallic selenium, 4.4 g of 4-chloroaniline, 2.36 g of potassium acetate, 3 g of the metal oxide mixture used in Example 1, 1.28 g of di-n-butylamine and 169 g of absolute ethanol were reacted together at 180° C. as described in Example 1. The reaction mixture was worked up as described in Example 1 and yielded 24.5 g of ethyl-N-(4-chlorophenyl)-carbamate, b.p. 118°–120° C./0.2 mm. The substance was 98.5% pure according to gas chromatographic analysis.

EXAMPLE 20

25.46 g of 2,4-dinitrotoluene, 1.96 g of potassium acetate, 0.2 g of metallic selenium, 3.5 g of 2,4-diaminotoluene, 2.5 g of the metal oxide mixture used in Example 1, 0.64 g of di-n-butylamine and 140 g of absolute ethanol were introduced into a 0.7 liter autoclave. The air in the autoclave was replaced by gaseous nitrogen and then by carbon monoxide. Carbon monoxide was then forced into the autoclave until the starting pressure of 100 bar was reached at room temperature. The reaction mixture was heated with stirring and maintained at 180° C. for one hour. Analysis by liquid chromatography of the filtrate separated from the selenium and metal oxide mixture indicated quantitative conversion of 2,4-dinitrotoluene. The filtrate contained 29.5 g of 2,4-diethoxycarbonyl-aminotoluene.

COMPARISON EXAMPLE 20a

Example 20 was repeated without using di-n-butylamine. The filtrate contained 22.9 g of 2,4-diethoxycarbonyl-aminotoluene.

EXAMPLE 21

Example 20 was repeated with the addition of 1 g of sulphur and using 140 g of methanol instead of ethanol. The reaction mixture was filtered hot to remove insoluble constituents and the filtrate was slowly cooled to −10° C. The crystalline paste which formed was filtered off and washed twice with 15 ml of cold methanol 20.5 g of dimethoxycarbonylaminotoluene, m.p. 167°–169° C., were obtained after drying.

COMPARISON EXAMPLE 21a

Example 21 was repeated without using di-n-butylamine. Working up of the reaction yielded 14.8 g of dimethoxycarbonylaminotoluene, m.p. 165°–167° C. The infrared spectra of the compounds isolated in Example 21 and Comparison Example 21a were identical.

EXAMPLE 22

40.0 g of 2,4-dinitrotoluene was converted quantitatively. The filtrate contained 43.2 g of 2,4-diethoxycarbonylaminotoluene.

EXAMPLE 23

Example 20 was repeated at 170° C. with the addition of 1.0 g of sulphur. 2,4-nitrotoluene was converted quantitatively. The filtrate contained 31.0 g of 2,4-diethoxycarbonylaminotoluene.

COMPARISON EXAMPLE 23a

Example 23 was repeated without using di-n-butylamine. The filtrate contained 20.2 g of 2,4-diethoxycarbonyl-aminotoluene.

EXAMPLE 24

20.8 g of nitrobenzene, 0.1 g of metallic selenium, 3.21 g of aniline, 2.36 g of potassium acetate, 3 g of a metal oxide mixture of iron-III oxide and vanadium pentoxide in proportions by weight of 11:1, 0.64 g of di-n-butylamine and 169 g of absolute ethanol were introduced into a 0.7 liter autoclave. The autoclave was rinsed with nitrogen and then with carbon monoxide. Carbon monoxide was then forced into the autoclave until the starting pressure of 100 bar was reached. The reaction mixture was heated to 170° C. with stirring and then stirred at 170° C. for one hour. Gas chromatographic analysis indicated quantitative conversion of nitrobenzene. The filtrate contained 26.9 g of ethyl-N-phenylcarbamate and 3.2 g of aniline.

COMPARISON EXAMPLE 24a

Example 24 was repeated without using di-n-butylamine. The filtrate contained 23.8 g of ethyl-N-phenylcarbamate and 3.5 g of aniline.

EXAMPLE 25

51 g of nitrobenzene, 0,5 g of metallic selenium, 12 g of aniline, 4 g of potassium acetate, 4 g of the metal oxide mixture of example 1, 1,28 g of di-n-butylamine and 300 g of absolute ethanol were introduced into a 1,3 l autoclave. The autoclave was rinsed with nitrogen and then with carbon monoxide. Carbon monoxide was then forced into the autoclave until the starting pressure of 120 bar was reached. The reaction mixture was heated to 150° C. with stirring and then stirred at 150° C. for two hours. Gas chromatographic analysis indicated quantative conversion of nitrobenzene. The filtrate contained 77.2 g of of ethyl-N-phenylcarbamate and 5,1 g of aniline.

EXAMPLE 26

42 g of nitrobenzene, 4 g of sulphur, 12 g of aniline, 2 g of potassium acetate, 4 g of metal oxide mixture consisting of iron-III-oxide and vanadium pentoxide in proportions by weight of 11:1, 1,28 g of di-n-butylamine and 300 g of absolute ethanol were reacted for two hours at 160° C. as described in Example 25. The nitrobenzene was quantatively converted. The filtrate contained 45,9 g of methyl-N-phenylcarbamate and 11.7 g of aniline.

What is claimed is:

1. A process for the preparation of aromatic urethanes by the reaction of aromatic nitro compounds with aliphatic, cycloaliphatic or araliphatic alcohols and carbon monoxide in the presence of,
   a. sulfur and/or selenium and/or compounds of these elements and
   b. aromatic amino compounds and/or aromatic urea compounds and,
   c. catalyst systems containing tertiary organic amines and/or alkali metal salts of weak acids, wherein said catalyst system additionally contains:
   d. oxidizing agents selected from the group consisting of oxygen, oxidizing organic compounds containing chemically bound oxygen and oxidizing inorganic compounds of metals of the 1st, 2nd, and 5th through 8th sub-Groups of the Periodic System of Elements containing chemically bound oxygen, and
   e. ammonia and/or aliphatic, araliphatic, cycloaliphatic or heterocyclic amines having at least one hydrogen atom bound to an amine nitrogen atom.

2. A process according to claim 1, wherein the substances used as component (e) are secondary amines.

3. A process according to claim 1, wherein the substance used as component (c) is diazabicyclo[2,2,2]-octane.

4. A process according to claim 1, wherein the substance used as component (c) is a tertiary amine in combination with a salt of the following general formula:

MeX wherein, Me represents an alkali metal cation and, X represents an iodide, cyanate or thiocyanate anion.

5. A process according to claim 1, wherein the aromatic nitro compound is nitrobenzene.

6. A process according to claim 1, wherein the aromatic nitro compound used is dinitrotoluene.

7. A process according to claim 1, wherein the alcohol used is ethyl alcohol or methyl alcohol.

* * * * *